US010639106B1

(12) United States Patent
Sheiner et al.

(10) Patent No.: US 10,639,106 B1
(45) Date of Patent: May 5, 2020

(54) CONTROLLING APPEARANCE OF DISPLAYED MARKERS FOR IMPROVING CATHETER AND TISSUE VISIBILITY

(71) Applicant: Biosense Webster (Israel) Ltd., Yokneam (IL)

(72) Inventors: Amiram Sheiner, Zichron Yaakov (IL); Assaf Cohen, Kiryat Bialik (IL); Ido Ilan, Yokneam (IL); Noam Seker Gafni, Irvine, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 16/415,159

(22) Filed: May 17, 2019

(51) Int. Cl.
| | |
|---|---|
| *A61B 5/00* | (2006.01) |
| *A61B 34/00* | (2016.01) |
| *A61M 25/01* | (2006.01) |
| *A61B 5/06* | (2006.01) |
| *A61B 5/0245* | (2006.01) |
| *G16H 40/63* | (2018.01) |
| *G06T 11/60* | (2006.01) |
| *A61B 18/14* | (2006.01) |
| *A61B 18/00* | (2006.01) |

(52) U.S. Cl.
CPC ............ *A61B 34/25* (2016.02); *A61B 5/0245* (2013.01); *A61B 5/062* (2013.01); *A61B 5/743* (2013.01); *A61M 25/0108* (2013.01); *G06T 11/60* (2013.01); *G16H 40/63* (2018.01); *A61B 18/1492* (2013.01); *A61B 2018/00351* (2013.01); *A61B 2018/00577* (2013.01); *G06T 2210/41* (2013.01)

(58) Field of Classification Search
None
See application file for complete search history.

(56) References Cited

U.S. PATENT DOCUMENTS

| | | |
|---|---|---|
| 5,391,199 A | 2/1995 | Ben-Haim |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 2002/0065455 A1 | 5/2002 | Ben-Haim et al. |
| 2003/0120150 A1 | 6/2003 | Govari |
| 2004/0068178 A1 | 4/2004 | Govari |
| 2011/0160593 A1* | 6/2011 | Deno ............... A61B 34/20 600/463 |
| 2011/0166407 A1* | 7/2011 | Sumanaweera ...... A61N 5/1077 600/1 |
| 2016/0128770 A1 | 5/2016 | Afonso et al. |
| 2017/0020395 A1 | 1/2017 | Malchano et al. |

(Continued)

FOREIGN PATENT DOCUMENTS

WO          9605768 A1     2/1996

*Primary Examiner* — Martin Mushambo

(57) ABSTRACT

A method for improving visualization of at least a catheter in an organ of a patient, the method includes displaying a map of the organ, and at least a first visual marker overlaid on the map. A position, falling within the map, of a distal end of the catheter is received. Displayed on the map are (i) the distal end of the catheter in accordance with the received position, and (ii) instead of the first visual marker, at least a second visual marker, which increases visibility of at least one of the map and the distal end, relative to the first visual marker.

12 Claims, 3 Drawing Sheets

(56) References Cited

U.S. PATENT DOCUMENTS

| | | |
|---|---|---|
| 2017/0128128 A1 | 5/2017 | Saba et al. |
| 2017/0172457 A1* | 6/2017 | Govari .................. A61B 5/055 |
| 2018/0064504 A1 | 3/2018 | Barley et al. |

* cited by examiner

CONTROLLING APPEARANCE OF DISPLAYED MARKERS FOR IMPROVING CATHETER AND TISSUE VISIBILITY

FIELD OF THE INVENTION

The present invention relates generally to medical devices, and particularly to methods and systems for increasing the visibility of medical devices and tissue during medical procedures.

BACKGROUND OF THE INVENTION

Various medical systems, such as cardiac ablation, display to a physician visual markers indicative of procedure-related medical parameters.

For example, U.S. Patent Application Publication 2016/0128770 describes a method and system for presenting information representative of lesion formation. The system comprises an electronic control unit (ECU). The ECU is configured to acquire a value for an ablation description parameter and/or a position signal metric, wherein the value corresponds to a location in the tissue. The ECU is further configured to evaluate the value, assign it a visual indicator of a visualization scheme associated with the parameter/metric corresponding to the value, and generate a marker comprising the visual indicator such that the marker is indicative of the acquired value.

U.S. Patent Application Publication 2018/0064504 describes a visualization apparatus for visualizing a quality of applying energy to an object. The quality of applying energy at a location on the object is visualized based on a) a provided image of the object and b) a provided quality value which is a depth value indicative of the depth to which the applied energy has altered the object, representing the quality of applying energy to the object at the location on the object.

U.S. Patent Application Publication 2018/0020395 describes image processing systems, which utilize various methods and processing algorithms for enhancing or facilitating visual detection and/or sensing modalities for images captured in vivo by an intravascular visualization and treatment catheter.

SUMMARY OF THE INVENTION

An embodiment of the present invention that is described herein provides a method for improving visualization of at least a catheter in an organ of a patient, the method includes displaying a map of the organ, and at least a first visual marker overlaid on the map. A position, falling within the map, of a distal end of the catheter is received. Displayed on the map are (i) the distal end of the catheter in accordance with the received position, and (ii) instead of the first visual marker, at least a second visual marker, which increases visibility of at least one of the map and the distal end, relative to the first visual marker.

In some embodiments, displaying the second visual marker, instead of the first visual marker, is performed in response to identifying that the position of the distal end is within a predefined vicinity of the first visual marker. In other embodiments, the method includes, upon identifying that the position of the distal end is no longer within the predefined vicinity, re-displaying the first visual marker instead of the second visual marker. In yet other embodiments, displaying the second visual marker, instead of the first visual marker, includes modifying at least an attribute of the first visual marker to produce the second visual marker.

In an embodiment, the attribute is selected from a list consisting of: dimension, shape, opacity and color. In another embodiment, the organ includes a heart, and the first and second visual markers are indicative of one or more parameters of radiofrequency (RF) ablation applied to tissue of the heart.

There is additionally provided, in accordance with an embodiment of the present invention, a system for improving visualization of at least a catheter in an organ of a patient, the system includes an output device and a processor. The processor is configured to (a) display, on the output device, a map of the organ and at least a first visual marker overlaid on the map, (b) receive a position, falling within the map, of a distal end of the catheter, and (c) display on the map (i) the distal end of the catheter in accordance with the received position, and (ii) instead of the first visual marker, at least a second visual marker, which increases visibility of at least one of the map and the distal end, relative to the first visual marker.

The present invention will be more fully understood from the following detailed description of the embodiments thereof, taken together with the drawings in which:

DETAILED DESCRIPTION OF EMBODIMENTS

Overview

Figure 1:
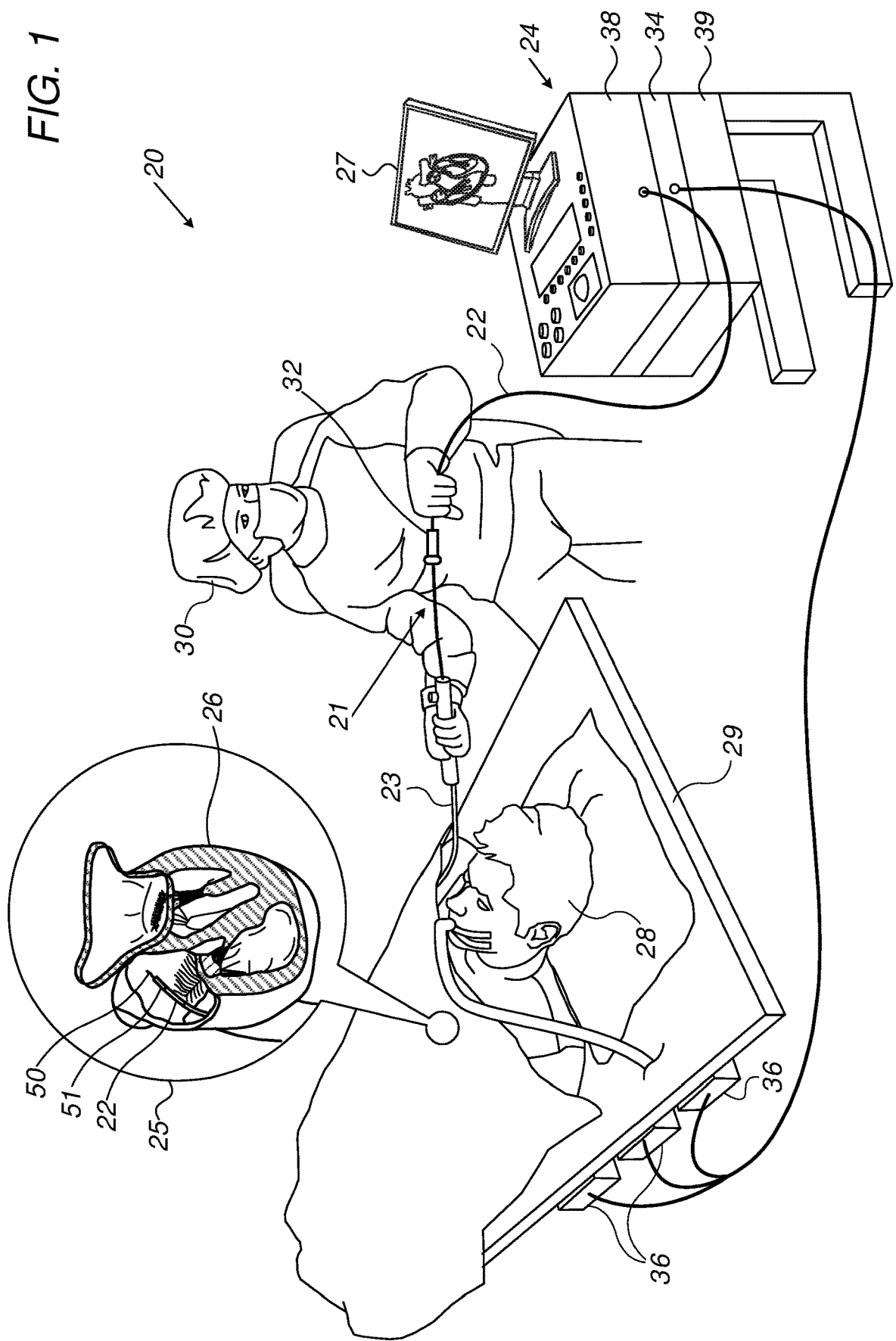
FIG. 1 is a schematic, pictorial illustration of a catheter-based magnetic position-tracking and ablation system, in accordance with an embodiment of the present invention.

Some medical systems, such as cardiac ablation systems, may display supplemental information on an operating display, for assisting the procedure workflow.

Embodiments of the present invention that are described hereinbelow provide methods and systems for increasing the visibility of a medical catheter and of tissue during a medical invasive procedure such as an ablation procedure. In some embodiments, a system that displays an ablation catheter in a patient's heart comprises a processor, which is electrically coupled to the ablation catheter, and an output device. In some embodiments, the processor is configured to display on the output device a map of at least part of the heart, and one or more visual markers, which are overlaid on the map and visualize ablation parameters, such as temperature, duration and/or contact force, applied to the heart tissue. The markers are typically displayed as opaque objects.

In some cases, the opaque markers may visually obstruct one or more sections of the medical catheter and/or some of the tissue, which are essential for performing the procedure.

In some embodiments, the processor is configured to receive electrical position signals, which are indicative of one or more positions of the catheter distal end within the heart, wherein at least one of the positions falls within the map boundaries. In some embodiments, the processor is configured to identify that the current position of the distal end is within a predefined vicinity of at least one of the opaque visual markers, meaning that the opaque visual marker may obstruct the visibility of at least a section of the distal end. In such embodiments, the processor is configured to modify the visual appearance of that opaque visual marker, e.g., by displaying a translucent (i.e., semi-transparent) visual marker instead of the opaque visual marker. By replacing the opaque visual marker with a translucent visual marker, a user of the ablation system can see the previously-obstructed sections through the marker, and is able to carry out the ablation procedure successfully.

In some practical cases, the display of visual markers may be important for the workflow of the ablation procedure. For example, displaying opaque visual markers may provide the user with information essential for performing the ablation procedure accurately. In some embodiments, after the user moves the distal end away from the aforementioned visual markers, the processor is configured to redisplay the one or more opaque visual markers, which were modified into translucent visual markers.

The disclosed techniques improve the patient safety and quality of ablation procedures, by providing physicians with procedure-assisting clear visual information, and improving the visibility of tissue and catheters used in the ablation procedure. Moreover, the disclosed techniques may be applied to any sort of tagging or other visual markers displayed on any anatomical map during any sort of medical procedure carried out on a patient organ.

System Description

FIG. 1 is a schematic, pictorial illustration of a catheter-based magnetic position-tracking and ablation system 20, in accordance with an embodiment of the present invention. System 20 comprises a catheter 21, having a shaft distal end 22 that is navigated by a physician 30 into an organ, in the present example a heart 26, of a patient 28 via the vascular system. In some embodiments, physician 30 inserts shaft distal end 22 through a sheath 23, while manipulating distal end 22 using a manipulator 32 located at the proximal end of catheter 21.

Reference is now made to an inset 25. In some embodiments, system 20 comprises a magnetic sensor 51, also referred to herein as a magnetic position tracking sensor or sensor 51 for brevity, and an ablation catheter 50, which are coupled to distal end 22.

In the embodiments, catheter 21 may be used for various procedures, such as electrophysiological (EP) mapping of heart 26 and for ablating selected tissue of heart 26.

In some embodiments, the proximal end of catheter 21 is electrically connected to a control console 24 via electrical leads and/or traces. In an embodiment, console 24 comprises a processor 39 and interface circuits 38, which is configured to exchange signals between processor 39 and various components and assemblies of system 20.

In some embodiments, interface circuits 38 are configured to receive electrical signals from catheter 21 and other sensors of system 20. Circuits 38 are further configured to send electrical signals from processor 38 to various components and assemblies of system 20, such as applying power via catheter 21 for ablating tissue of heart 26, and for controlling the other components and assemblies of system 20.

In some embodiments, system 20 comprises multiple (e.g., three) magnetic field generators 36, configured to produce alternating magnetic fields. Field generators 36 are placed at known positions external to patient 28, for example, below a patient table 29.

In some embodiments, console 24 further comprises a driver circuit 34, which is configured to drive magnetic field generators 36, and an output device, in the present example a display 27.

During a medical procedure physician 30 navigates distal end 22 of catheter 21 in heart 26. In some embodiments, in response to the magnetic fields irradiated from field generators 36, magnetic sensor 51 is configured to produce a differential electrical signal, also referred to herein as a differential signal or a position signal, indicative of the current position of distal end 22 in heart 26.

In some embodiments, based on the differential signal received from sensor 51, processor 39 is configured to display, e.g., on display 27, the current position of distal end 22 in the coordinate system of system 20.

This method of position sensing is implemented, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Processor 39 typically comprises a general-purpose processor, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

Displaying Visual Markers Overlaid on Heart Map

Figure 2:
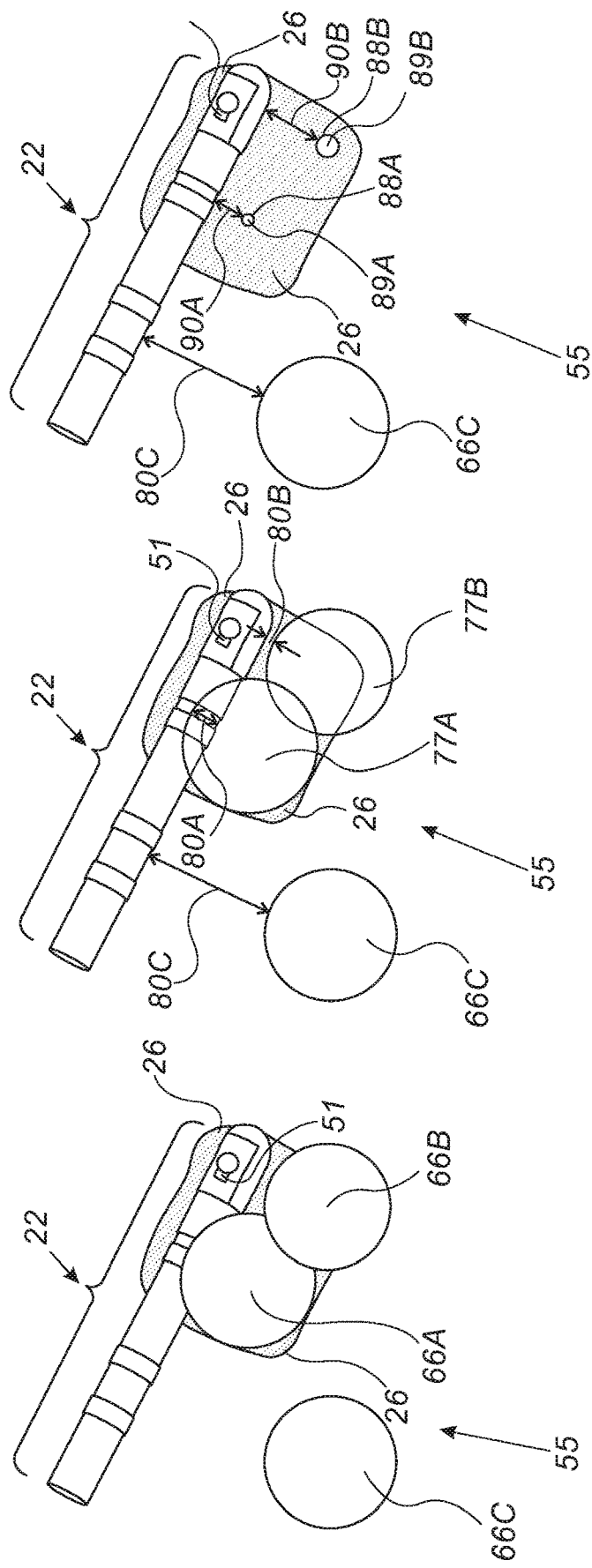
FIGS. 2A, 2B and 2C are schematic, pictorial illustrations of a catheter and visual markers overlaid on a map of an organ, in accordance with embodiments of the present invention.

FIG. 2A is a schematic, pictorial illustration of an anatomical map 55 of heart 26, in accordance with an embodiment of the present invention. In some embodiments, processor 39 is configured to display one or more visual markers, such as visual markers 66A, 66B and 66C, overlaid on anatomical map 55, also referred to herein as map 55 for brevity. In the context of the present invention and in the claims, the term "visual marker" refers to any sort of tag, displayed, e.g., by processor 39 on display 27, so as to provide physician 30 with supplemental information that may assist physician 30 in navigating and positioning distal end 22 in tissue of heart 26, as will be described in detail below.

In some embodiments, the dimension and shape of visual markers 66A, 66B and 66C may be indicative of the respective dimension and shape of the lesion formed by ablating tissue of heart 26. In such embodiments, the attributes of visual markers 66A, 66B and 66C, such as color, shape, and dimension, may be determined by ablation parameters applied to the tissue of heart 26, such as but not limited to ablation energy, duration, contact force and temperature.

In some embodiments, processor 39 is configured to display distal end 22 of catheter 21 in map 55. In the example of FIG. 2A, visual markers 66A, 66B and 66C are opaque and have a round shape. Therefore, visual markers 66A and 66B may obstruct the visibility of at least sections of distal end 22 and of tissue of heart 26, but visual marker 66C is sufficiently far from and therefore does not obscure the tissue of interest and/or distal end 22. Note that in order to perform electrophysiological (EP) mapping, and/or tissue ablation procedure, it is important for physician 30, to have high visibility of both distal end 22 and the ablated tissue of heart 26.

Increasing Visibility of Catheter Distal-End and Cardiac Tissue During Ablation Procedure FIG. 2B is a schematic, pictorial illustration of anatomical map 55 of heart 26, in accordance with another embodiment of the present invention. In some embodiments, after inserting catheter 21 into the body of patient 28, processor 39 is configured to receive position signals indicative of the current position of distal end 22, e.g., in heart 26. Processor 39 may receive the position signals from position sensor 51 of the magnetic position tracking system, as described in FIG. 1 above, or from any other suitable source.

In some embodiments, processor 39 is configured to estimate the distance between the positions of distal end 22 and each of the visual markers displayed on map 55. The distance may be the minimal distance between the nearest edges of distal end 22 and the respective visual marker, or any other suitable calculated distance. In the example of FIG. 2B, processor 39 is configured to estimate a distance 80A, which is the minimal distance between distal end 22 and visual marker 77A. Similarly, processor 39 is configured to estimate a distance 80B between distal end 22 and visual marker 77B, and a distance 80C between distal end 22 and visual marker 66C.

In some embodiments, processor 39 holds a threshold distance, indicative of the allowed proximity between the visual marker and distal end 22. In response to identifying that the current position of distal end 22 is within a predefined vicinity of the visual marker, processor 39 is configured to modify at least one attribute of the visual marker, so as to increase the visibility of distal end 22. The attributes may comprise dimension, shape, opacity, color, position or any other suitable attribute.

The modify in dimension, which is depicted for example in FIG. 2C below, may be lateral, e.g., on the surface of heart 26, and/or in the depth of the tissue of heart 26. The shape may be modified from round to elliptical or any other suitable shape. The change in position may be used in one or more visual markers, so as to visualize a specific tissue of heart 26 (e.g., ostium of pulmonary vein) or a specific element of distal end 22 (e.g., an ablation electrode). The change in opacity will be described in detail in the following example, and is shown in FIG. 2B.

For example, distances 80A and 80B are below the aforementioned threshold distance stored in processor 39. In some embodiments, processor 39 is configured to display translucent visual markers 77A and 77B, instead of opaque visual markers 66A and 66B, and thereby, to improve the visibility of distal end 22 and the tissue of heart 26. In an embodiment, visual markers 66A and 77A have substantially similar position, size and shape, but different level of transparency, which allows the improved visibility of distal end 22 and the tissue of heart 26, which are within the vicinity of visual marker 77A.

Note that distance 80C is larger than the threshold distance, in other words distal end 22 is not within the predefined vicinity of visual marker 66C. In this embodiment, processor 39 is configured to continue displaying opaque visual marker 66C in map 55.

Moreover, during the ablation procedure, physician 30 may move distal end 22 away from visual markers 77A and 77B. In some embodiments, upon identifying that the current position of distal end 22 is no longer within the predefined vicinity of visual markers 77A and 77B, processor 39 is configured to re-display at least one of opaque visual markers 66A and 66B instead of translucent visual markers 77A and 77B.

FIG. 2C is a schematic, pictorial illustration of anatomical map 55 of heart 26, in accordance with an alternative embodiment of the present invention. In some embodiments, instead of displaying visual markers 66A and 66B that obstruct the visibility of distal end 22, as shown in FIG. 1 above, processor 39 is configured to display at the same respective positions, visual markers 88A and 88B.

As described for visual markers 77A and 77B in FIG. 2A above, in the example of FIG. 2C, visual markers 88A and 88B may be based on visual markers 66A and 66B with a modification of one or more attributes.

In some embodiments, visual marker 88A may have a round shape, similar to visual marker 66A, but a smaller diameter therefrom. By reducing the diameter of the visual marker, a minimal distance 90A between the edges of distal end 22 and visual marker 88A, is larger than the predefined threshold described in FIG. 2B above. In this configuration, distal end 22 is not within the predefined vicinity of visual marker 88A, which increases the visibility of at least one of the map of heart 26 and distal end 22, relative to visual marker 66A. In some embodiments, processor 39 is configured to estimate the distance between a center of gravity (COG) 89A and the nearest edge of distal end 22, and based on the estimated distance, to adjust the diameter of visual marker 88A, so as to have distance 90A equal to or larger than the predefined threshold distance stored in processor 39.

In some embodiments, processor 39 is configured to display visual marker 88B on map 55, by setting a COG 89B and the diameter of visual marker 88B so that a minimal distance 90B, between distal end 22 and visual marker 88B, is larger than the predefined threshold distance stored in processor 39.

As described in FIG. 2B above, visual marker 66C is sufficiently far from distal end 22 and therefore processor 39 may not display another visual marker instead of visual marker 66C.

In the exemplary configuration shown in FIG. 2C, visual markers 88A, 88B and 66C have a round shape but different respective diameters so as to increase the visibility of at least one of map 55 and distal end 22, relative to visual markers 66A and 66B. In other embodiments, processor 39 is configured to modify the penetration depth of the displayed visual marker in the tissue of heart 26. The change in depth may improve the aforementioned visibility when physician 30 may rotate map 55 so as to view the tissue of heart 26 from a different perspective. In such embodiments, processor 39 is configured to set a symmetrically round shape of the visual marker, or may form an elliptical-shape visual marker for visualizing, in a selected dimension, a specific tissue of heart 26 or a specific element of distal end 22.

In other embodiments, processor 39 is configured to set a similar diameter to all visual markers overlaid on map 55. For example, in the configuration of FIG. 2C, processor may set the diameter of visual marker 88A, also to visual markers 88B and 66C.

Additionally or alternatively, processor 39 is configured to modify the shape and/or opacity and/or COG of one or more of the visual markers displayed in map 55. Moreover, processor 39 is configured to temporarily remove one or more visual markers from map 55. Note that at least some of the visual markers are used in the workflow of the medical procedure, therefore, processor 39 may not remove or shift any visual marker that is essential for the workflow of the medical procedure.

Additionally or alternatively, processor 39 is configured to temporarily shift the COG of a visual marker that may come across the moving direction of distal end 22 across map 55. Note that in case the visual marker is essential for the workflow of the medical procedure, processor 39 may not shift or temporarily remove the respective visual marker from map 55.

In other embodiments, the visual markers shown in FIGS. 2A-2C, may be indicative of any parameter other than the ablation parameters described above. For example, electropotential sensed in tissue of heart 26 by electrodes mounted on distal end 22, or estimated lesion size based on ablation parameters to be applied to heart 26, or any other suitable parameter. In such embodiments, by modifying the display of the visual markers, processor may assist physician 30 with the navigation and placement of distal end 22 in a densely pre-ablated tissue of heart 26.

In other embodiments, processor 39 or any other processor connected to system 20, may display the visual markers on any output device other than display 27. For example, physician 30 may use augmented reality (AR) goggles configured to display the visual markers and/or related information overlaid on map 55 and/or on any suitable anatomical image of heart 26. Additionally or alternatively, the display of the visual markers may be implemented using any other suitable technique.

This particular configuration of the displayed visual markers is shown in FIGS. 2A-2C by way of example, in order to illustrate certain problems that are addressed by embodiments of the present invention and to demonstrate the application of these embodiments in enhancing the visualization of distal end 22 and selected tissue of heart 26. Embodiments of the present invention, however, are by no means limited to this specific sort of example configurations, and the principles described herein may similarly be applied to other sorts of user interfaces and display systems.

Figure 3:
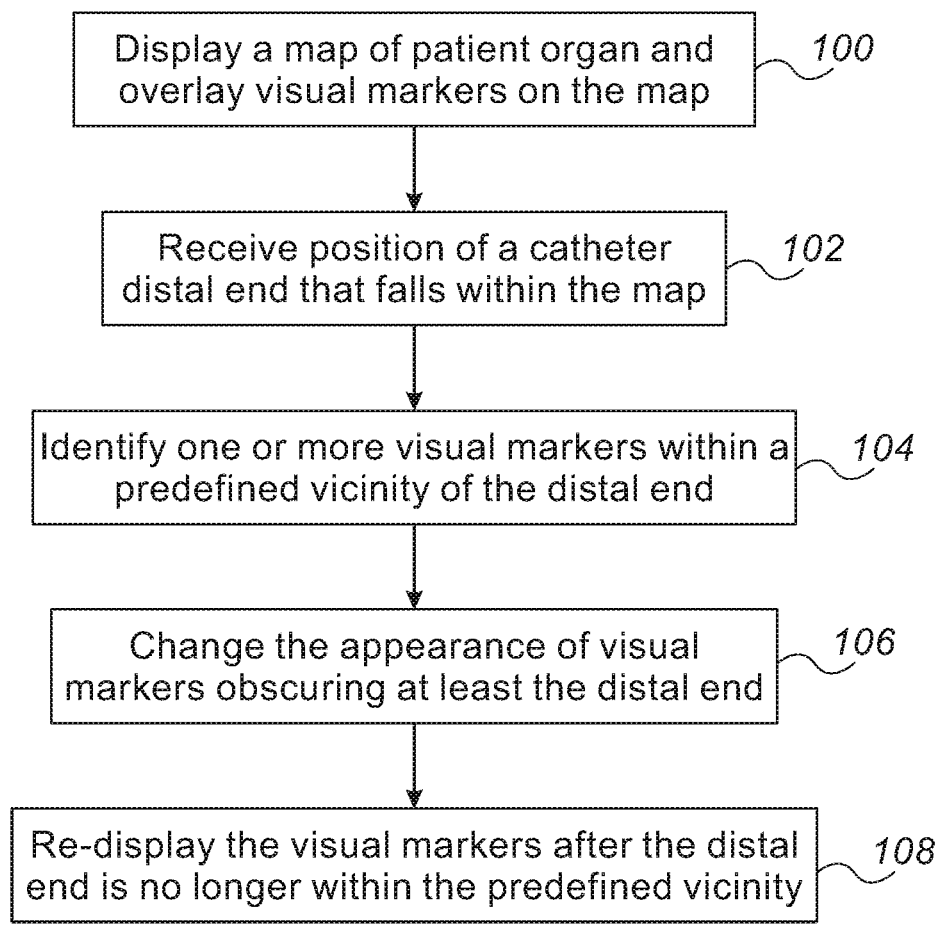
FIG. 3 is a flow chart that schematically illustrates a method for increasing visibility of tissue and a catheter in a map having visual markers, in accordance with an embodiment of the present invention.

A Method for Improving Visualization of Catheter Distal-End During Electrophysiological Procedure FIG. 3 is a flow chart that schematically illustrates a method for increasing visibility of heart 26 and distal end 55 of catheter 21 during an electrophysiological procedure, in accordance with an embodiment of the present invention.

The method begins at a first displaying step 100, in which processor 39 displays on an output device, such as display 27, map 55 of heart 26 or any other organ of patient 28. In some embodiments, processor 39 overlays one or more visual markers, such as visual markers 66A-66C on map 55.

At a position receiving step 102, processor 39 receives, from sensor 51 of the magnetic position tracking system, signal indicative of the current position of distal end 22, which is navigated by physician 30 or by any other suitable operator of system 20. In some embodiments, at least some of the signals are indicative of one or more positions that fall within the boundaries of map 55.

At a proximity identification step 104, processor 39 may identify one or more visual markers, such as visual markers 66A and 66B, within a predefined vicinity of distal end 22. In some embodiments, processor 39 may hold a threshold distance or a set of criteria and/or algorithms that determine the aforementioned predefined vicinity.

At a visual marker modifying step 106, processor 39 may modify the visual appearance of at least some of the visual markers identified in step 104. For example, processor 39 may display translucent visual markers 77A and 77B instead of opaque visual markers 66A and 66B, which may otherwise obscure at least a section of distal end 22 or tissue of heart 26 that is essential for the workflow of the medical procedure.

Note that in the context of the present invention and in the claims, the sentences "modify the visual appearance of at least some of the visual markers," "display translucent visual markers 77A and 77B instead of opaque visual markers 66A and 66B" and the claim language "displaying the second visual marker, instead of the first visual marker" refer to the same technique applied by processor 39 to visual markers 66A and 66B, so as to improve the visualization of distal end 22 and tissue of heart 26, as described for example in FIG. 2B above.

At a second displaying step 108 that concludes the method, after distal end 22 is moved away from map 55, and therefore is no longer within the predefined vicinity of the modified visual markers, processor 39 may redisplay the visual markers as described in step 100 above. In other words, when distal end 55 is in close proximity to one or more given visual markers, processor 39 may modify the visual appearance (e.g., opaqueness and size) of the one or more given visual markers, as described step 106 above, but after distal end 22 is moved to a sufficiently large distance from the given visual markers, processor 39 may redisplay the original visual appearance of the one or more given visual markers. For example, at least one of the visual markers may be increased in size or opacity.

Although the embodiments described herein mainly address electrophysiological (EP) mapping and cardiac ablation procedures, the methods and systems described herein can also be used in any other minimally invasive medical application having tissue and/or medical tool located at a region of interest, which is obstructed by visual markers. Moreover, the embodiments described herein may be used in any application having an operator navigating through any given space and attempting to perform an operation in one specific narrow region of interest. The disclosed techniques may be applied to any visual obstructions related to the region of interest.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for improving visualization of at least a catheter in an organ of a patient, the method comprising:
    displaying a map of the organ, and at least a first visual marker overlaid on the map;
    receiving a position, falling within the map, of a distal end of the catheter; and
    displaying on the map (i) the distal end of the catheter in accordance with the received position, and (ii) instead of the first visual marker, at least a second visual marker, which increases visibility of at least one of the map and the distal end, relative to the first visual marker.

2. The method according to claim 1, wherein displaying the second visual marker, instead of the first visual marker, is performed in response to identifying that the position of the distal end is within a predefined vicinity of the first visual marker.

3. The method according to claim 2, and comprising, upon identifying that the position of the distal end is no longer within the predefined vicinity, re-displaying the first visual marker instead of the second visual marker.

4. The method according to claim 1, wherein displaying the second visual marker, instead of the first visual marker, comprises modifying at least an attribute of the first visual marker to produce the second visual marker.

5. The method according to claim 4, wherein the attribute is selected from a list consisting of: dimension, shape, opacity and color.

6. The method according to claim 1, wherein the organ comprises a heart, and wherein the first and second visual markers are indicative of one or more parameters of radiofrequency (RF) ablation applied to tissue of the heart.

7. A system for improving visualization of at least a catheter in an organ of a patient, the system comprising:
   an output device; and
   a processor, which is configured to:
      display, on the output device, a map of the organ and at least a first visual marker overlaid on the map;
      receive a position, falling within the map, of a distal end of the catheter; and
      display on the map (i) the distal end of the catheter in accordance with the received position, and (ii) instead of the first visual marker, at least a second visual marker, which increases visibility of at least one of the map and the distal end, relative to the first visual marker.

8. The system according to claim 7, wherein the processor is configured to display the second visual marker instead of the first visual marker, in response to identifying that the position of the distal end is within a predefined vicinity of the first visual marker.

9. The system according to claim 8, and comprising, upon identifying that the position of the distal end is no longer within the predefined vicinity, the processor is configured to re-display the first visual marker instead of the second visual marker.

10. The system according to claim 7, wherein the processor is configured to produce the second visual marker by modifying at least an attribute of the first visual marker.

11. The system according to claim 10, wherein the processor is configured to select the attribute from a list consisting of: dimension, shape, opacity and color.

12. The system according to claim 7, wherein the organ comprises a heart, and wherein the first and second visual markers are indicative of one or more parameters of radiofrequency (RF) ablation applied to tissue of the heart.

* * * * *